(12) United States Patent
Jackson et al.

(10) Patent No.: US 9,044,035 B2
(45) Date of Patent: Jun. 2, 2015

(54) REMELTED INGESTIBLE PRODUCTS

(75) Inventors: Thaddeus J. Jackson, High Point, NC (US); Frank Kelley St. Charles, Bowling Green, KY (US)

(73) Assignee: R.J. Reynolds Tobacco Company, Winston-Salem, NC (US)

(*) Notice: Subject to any disclaimer, the term of this patent is extended or adjusted under 35 U.S.C. 154(b) by 98 days.

(21) Appl. No.: 13/448,781

(22) Filed: Apr. 17, 2012

(65) Prior Publication Data

US 2013/0274296 A1 Oct. 17, 2013

(51) Int. Cl.
| | |
|---|---|
| A61K 8/00 | (2006.01) |
| A23G 3/34 | (2006.01) |
| A24B 13/00 | (2006.01) |
| A24B 15/16 | (2006.01) |
| A23G 3/38 | (2006.01) |
| A23G 3/42 | (2006.01) |
| A23G 3/48 | (2006.01) |
| A61K 31/455 | (2006.01) |

(52) U.S. Cl.
CPC .............. *A23G 3/0014* (2013.01); *A24B 13/00* (2013.01); *A24B 15/16* (2013.01); *A23G 3/38* (2013.01); *A23G 3/42* (2013.01); *A23G 3/48* (2013.01); *A61K 31/455* (2013.01)

(58) Field of Classification Search
None
See application file for complete search history.

(56) References Cited

U.S. PATENT DOCUMENTS

| | | | |
|---|---|---|---|
| 3,114,642 A | 12/1963 | Meisel | |
| 3,438,787 A | 4/1969 | DuRoss | |
| 3,738,845 A | 6/1973 | Liebrand | |
| 4,452,825 A | 6/1984 | Klacik et al. | |
| 4,806,356 A | 2/1989 | Shaw | |
| 4,967,773 A | 11/1990 | Shaw | |
| 5,098,730 A | 3/1992 | Pepper et al. | |
| 5,110,605 A | 5/1992 | Acharya | |
| 5,314,701 A | 5/1994 | Mentink et al. | |
| 5,362,496 A | 11/1994 | Baker et al. | |
| 5,549,906 A | 8/1996 | Santus | |
| 5,593,684 A | 1/1997 | Baker et al. | |
| 5,629,042 A | 5/1997 | Serpelloni et al. | |
| 5,656,284 A | 8/1997 | Balkin | |
| 5,733,574 A | 3/1998 | Dam | |
| 5,840,334 A | 11/1998 | Raiden et al. | |
| 5,869,098 A | 2/1999 | Misra et al. | |
| 6,083,531 A | 7/2000 | Humbert-Droz et al. | |
| 6,183,775 B1 | 2/2001 | Ventouras | |
| 6,221,392 B1 | 4/2001 | Khankari et al. | |
| 6,248,760 B1 | 6/2001 | Wilhelmsen | |
| 6,264,981 B1 | 7/2001 | Zhang et al. | |
| 6,280,761 B1 | 8/2001 | Santus | |
| 6,541,034 B1 | 4/2003 | Gergely et al. | |
| 6,586,449 B1 | 7/2003 | Walling | |
| 6,676,959 B1 | 1/2004 | Andersson et al. | |
| 6,828,336 B2 | 12/2004 | Walling | |
| 6,849,286 B1 | 2/2005 | Bayerköhler et al. | |
| 6,872,405 B2 | 3/2005 | Takaishi et al. | |
| 6,890,559 B1 | 5/2005 | Bayerköhler et al. | |
| 7,122,198 B1 | 10/2006 | Singh et al. | |
| 7,374,779 B2 | 5/2008 | Chen et al. | |
| 8,343,532 B2 | 1/2013 | Dam et al. | |
| 8,501,164 B2 | 8/2013 | Chen | |
| 8,545,870 B2 | 10/2013 | Dupinay et al. | |
| 2001/0016593 A1 | 8/2001 | Wilhelmsen | |
| 2003/0215553 A1 | 11/2003 | Ribadeau-Dumas et al. | |
| 2004/0052851 A1 | 3/2004 | Graff et al. | |
| 2004/0076665 A1 | 4/2004 | Graff et al. | |
| 2004/0101543 A1 | 5/2004 | Liu et al. | |
| 2004/0253307 A1 | 12/2004 | Hague et al. | |
| 2006/0120974 A1 | 6/2006 | Mcneight | |
| 2006/0171969 A1 | 8/2006 | Macelloni et al. | |
| 2006/0191548 A1 | 8/2006 | Strickland et al. | |
| 2007/0269386 A1 | 11/2007 | Steen et al. | |
| 2007/0269492 A1 | 11/2007 | Steen et al. | |
| 2008/0020050 A1 | 1/2008 | Chau et al. | |
| 2008/0286340 A1 | 11/2008 | Andersson et al. | |
| 2008/0286341 A1 | 11/2008 | Andersson et al. | |
| 2009/0004248 A1 | 1/2009 | Bunick et al. | |
| 2009/0014018 A1 | 1/2009 | Sengupta et al. | |
| 2009/0081291 A1 | 3/2009 | Gin et al. | |
| 2009/0263544 A1 | 10/2009 | Soldani | |
| 2009/0293889 A1 | 12/2009 | Kumar et al. | |
| 2010/0003309 A1 | 1/2010 | Quiroga | |
| 2010/0004294 A1 | 1/2010 | Axelsson et al. | |
| 2010/0124560 A1 | 5/2010 | Hugerth et al. | |
| 2011/0139164 A1* | 6/2011 | Mua et al. ..................... 131/111 |
| 2011/0220130 A1 | 9/2011 | Mua et al. | |
| 2012/0244104 A1 | 9/2012 | Mehta et al. | |
| 2013/0078307 A1* | 3/2013 | Holton et al. ................. 424/490 |

FOREIGN PATENT DOCUMENTS

| | | |
|---|---|---|
| WO | WO 2006/114604 | 11/2006 |
| WO | WO 2008/112124 | 9/2008 |
| WO | WO 2010/044736 | 4/2010 |

* cited by examiner

*Primary Examiner* — Snigdha Maewall
(74) *Attorney, Agent, or Firm* — Womble Carlyle Sandridge & Rice, LLP

(57) ABSTRACT

A method of preparing an orally ingestible hard boiled product, comprising: i) heating a sugar material to a first temperature sufficient to liquefy the sugar material; ii) cooling the liquefied sugar material to provide a cooled sugar material having a solid or semi-solid form; iii) heating the cooled sugar material to a second temperature, which is lower than the first temperature; iv) combining the sugar material with one or more temperature sensitive ingredients before, during, or after said heating step iii), but after said cooling step ii), such that an intimate mixture of the second liquefied sugar material and the one or more temperature sensitive ingredients is provided; and v) cooling the intimate mixture to form an orally ingestible product. Orally ingestible hard boiled products prepared according to this method are also provided.

38 Claims, 2 Drawing Sheets

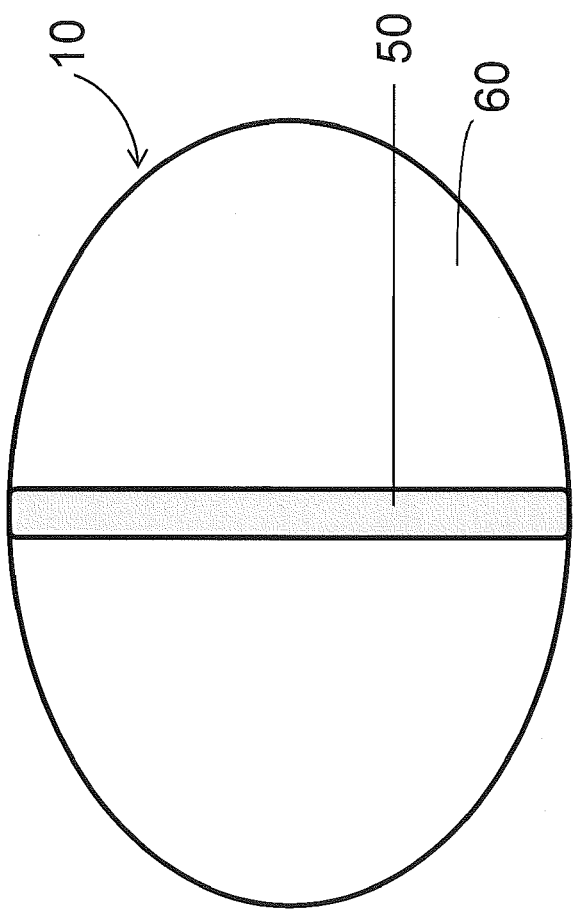

REMELTED INGESTIBLE PRODUCTS

FIELD OF THE INVENTION

The present invention relates to orally ingestible products comprising sugar, a sugar substitute, or a combination thereof, which are intended for human consumption. In particular, the invention relates to orally ingestible products that are derived from or that otherwise incorporate tobacco or a component thereof.

BACKGROUND OF THE INVENTION

Hard boiled sugar-based and sugar substitute-based orally ingestible products are generally amorphous products, having a relatively smooth and often glassy surface. The specific components of such products can be varied to provide a product with the desired texture, taste, appearance, and optional active ingredient concentration.

Orally ingestible hard boiled products can serve various purposes and are found in a range of industries. For example, some such products are found in the food industry (e.g., hard confectionary products of various forms and flavors), in the pharmaceutical industry (e.g., cough drops and nicotine-containing lozenges), and in the tobacco industry (e.g., smokeless tobacco lozenges).

Orally ingestible hard boiled products typically comprise a sugar and/or sugar substitute as a major component. For example, many hard boiled products comprise sugar and/or isomalt, although other sugar substitutes can be used. Although the specific method by which various ingestible hard boiled products are produced can vary, the process generally comprises heating the components at a temperature sufficient to melt the sugar and/or sugar substitute or a solution thereof. The resulting hot syrup generally serves as the base (i.e., the primary component) of the product.

Other ingredients can be added at various stages of this manufacturing process. For example, flavorings (e.g., natural and synthetic oils and extracts) and other components are often added to provide the product with the desired aroma and/or flavor. Food colorings/dyes can be added to alter the visual appearance of the product. Buffers and/or pH adjusters (i.e., acids or bases) are often added to ensure that the acidity of the product is within a desired range. Where relevant, active ingredients (e.g., cough suppressants, vitamins, minerals, drugs, or nicotine) are also added.

To ensure that all ingredients are thoroughly mixed throughout the final product, the ingredients are typically added to the mixture at a somewhat elevated temperature in the manufacturing process (i.e., when the base of the ingestible product is still in a liquid state). However, certain ingredients are volatile components that can evaporate when added at an elevated temperature. Further, certain ingredients can decompose at elevated temperatures. For example, sodium bicarbonate readily decomposes into sodium carbonate, water, and carbon dioxide at temperatures in excess of 70° C. and, thus, generally cannot be used because of the extended mixing times and the high temperatures at which such mixtures are typically maintained to ensure complete mixing. Additionally, certain ingredients can impact the final product in other ways when added at elevated temperatures. For example, adding food colors to hot sucrose-containing syrup can result in inversion of the sucrose, arising from reaction between the acid in food color and the sucrose. Mixtures of sucrose and acid in the presence of heat can produce dextrose and fructose, which alters the nature of the resulting orally ingestible hard boiled product.

Consequently, it would be desirable to provide a method by which certain ingredients could be incorporated within a hard boiled product without causing undesirable changes in the composition, such as through evaporation or decomposition of certain ingredients or formation of byproducts.

SUMMARY OF THE INVENTION

The present invention provides a method of preparing an orally ingestible hard boiled product as well as the products prepared thereby. The method can, in some embodiments, provide for decreased exposure of certain temperature sensitive ingredients to extended heating times and/or elevated heating temperatures. Such methods advantageously may decrease decomposition and/or evaporation of such ingredients as compared with traditional processing techniques, which may require incorporation of the ingredients at higher temperatures and/or involve exposure to elevated temperatures for longer periods of time. Such methods may provide for the preparation of hard boiled products that display desirable characteristics associated with hard boiled products (e.g., a glassy appearance). Typically, the hard boiled products include about 40% or more by weight or about 50% by more by weight of a sugar material. More often, the hard boiled products include a sugar material in an even higher amount, such as about 80% or more by weight or about 90% or more by weight.

In certain aspects, the present invention provides a method of preparing an orally ingestible product, comprising: i) heating a sugar material to a first temperature sufficient to liquefy the sugar material and form a first liquefied sugar material; ii) cooling the first liquefied sugar material to provide a cooled sugar material having a solid or semi-solid form; iii) heating the cooled sugar material to a second temperature, which is lower than the first temperature, to provide a second liquefied sugar material; iv) combining the sugar material with one or more temperature sensitive ingredients before, during, or after said heating step iii), but after said cooling step ii), such that an intimate mixture of the second liquefied sugar material and the one or more temperature sensitive ingredients is provided; and v) cooling the intimate mixture to form an orally ingestible product.

In certain embodiments, the method may further comprise the step of subdividing the cooled sugar material of step ii) into a plurality of pieces, and the combining step may further comprise mixing the subdivided, cooled sugar material with the one or more temperature sensitive ingredients. The step of subdividing the cooled sugar material may, for example, comprise grinding the cooled sugar material to provide a particulate material.

In other aspects, the invention provides a method of preparing an orally ingestible product, comprising: i) heating a sugar material to a first temperature sufficient to liquefy the sugar material and form a liquefied sugar material; ii) cooling the liquefied sugar material to provide a cooled sugar material having a solid or semi-solid form; iii) subdividing the cooled sugar material into a plurality of pieces; iv) combining the subdivided sugar material with one or more temperature sensitive buffering agents to form a mixture; v) heating the mixture to a second temperature, which is lower than the first temperature, to provide a liquefied intimate mixture of the sugar material and the one or more temperature sensitive buffering agents; and vi) cooling the intimate mixture to form an orally ingestible product.

The first and second temperatures of the methods can vary. In some embodiments, the first temperature is a temperature at or above the hard crack stage of the sugar material. In some embodiments, the first temperature is about 150° C. to about 170° C. The second temperature can be, in some embodiments, about 60° C. to about 150° C. or about 60° C. to about 120° C. The difference between the first and second temperatures can be, for example, at least about 10° C.; at least about 30° C.; or at least about 50° C. In one particular embodiment, the first temperature is about 150° C. to about 170° C., the second temperature is about 60° C. to about 150° C., and the difference between the first temperature and the second temperature is at least about 10° C. (e.g., at least about 30° C.).

In further aspects, the invention provides a method of preparing an orally ingestible product, comprising: i) applying heat to a sugar material sufficient to liquefy the sugar material and form a first liquefied sugar material; ii) cooling the first liquefied sugar material to provide a cooled sugar material having a solid or semi-solid form; iii) applying heat to the cooled sugar material to provide a second liquefied sugar material, the amount of heat applied to the cooled sugar material being less than the amount of heat applied in step i); iv) combining the sugar material with one or more temperature sensitive ingredients before, during, or after said step of applying heat to the cooled sugar material iii), but after said cooling step ii), such that an intimate mixture of the second liquefied sugar material and the one or more temperature sensitive ingredients is provided; and v) cooling the intimate mixture to form an orally ingestible product.

In such methods, in some embodiments, the step of applying heat to a sugar material in step i) comprises heating the sugar material at or above the hard crack stage of the sugar material. In certain embodiments, the difference in heat applied in step i) and step iii) is characterized by a difference in temperature of the material heated in each step of at least about 10° C. For example, in some embodiments, the difference in temperature of the material heated in each step is at least about 30° C.

In some embodiments, the sugar material in any of the methods provided herein comprises a sugar alcohol. For example, the sugar material may comprise isomalt. The method may, in some embodiments, further comprise the step of introducing the intimate mixture into a mold prior to cooling such that the orally ingestible product is formed into a desired shape.

The types of temperature sensitive ingredients combined with the sugar material can vary. In certain embodiments, the one or more temperature sensitive ingredients are selected from the group consisting of buffering agents, flavorings, pharmaceutically active ingredients, and combinations thereof. For example, in some embodiments, the temperature sensitive ingredient is a carbonate buffering agent or a nicotinic compound. In certain embodiments, the temperature sensitive ingredient is sodium carbonate, sodium bicarbonate, or a combination thereof. Where a nicotinic compound is provided, it may be, for example, in the form of a nicotine salt. The nicotinic compound may, in some embodiments, be sorbed onto a porous particulate carrier.

The intimate mixture provided in the methods of the invention can comprise other components; for example, in some embodiments, the intimate mixture further comprises a tobacco material. In such embodiments, the tobacco material can comprise a tobacco extract or particulate tobacco. The orally ingestible product can, therefore, be in the form of a smokeless tobacco product.

In certain embodiments, the orally ingestible product is formed by combining the liquefied intimate mixture comprising the temperature sensitive buffering agent with a second non-buffered composition comprising a sugar material to form a multi-layered product. For example, in some embodiments, the intimate mixture and the second non-buffered composition are combined in liquefied form and then cooled to form the multi-layered product. In some embodiments, both the intimate mixture comprising the temperature sensitive buffering agent and the second non-buffered composition of the multi-layered product are exposed on the surface of the product. In some embodiments, one or both of the intimate mixture comprising the temperature sensitive buffering agent and the second non-buffered composition further comprise a pharmaceutically active ingredient. In some embodiments, one or both of the intimate mixture comprising the temperature sensitive buffering agent and the second non-buffered composition further comprise a tobacco material.

In another aspect of the invention is provided an orally ingestible product prepared according to any of the methods provided herein. The form of the product can vary; for example, in some embodiments, the orally ingestible product is in the form of a confectionary, a pharmaceutical composition, or a smokeless tobacco product.

In certain aspects, the invention provides an orally ingestible hard boiled product comprising: a) a buffered portion comprising a first sugar material and a buffering agent; and b) an unbuffered portion comprising a second sugar material, which may be the same as or different than the first sugar material. In some embodiments, the buffered portion is fully encapsulated by the unbuffered portion. In some embodiments, both the buffered portion and the unbuffered portion are exposed on the surface of the product. In certain embodiments, the buffered portion is in particulate form dispersed within the unbuffered portion. The unbuffered portion can be, for example, transparent or translucent and the buffered portion can be, for example, non-transparent or opaque.

In some embodiments, one or both of the buffered and unbuffered portions comprise a pharmaceutically active ingredient. For example, in certain embodiments, the pharmaceutically active ingredient is a nicotinic compound. In some embodiments, one or both of the buffered and unbuffered portions comprise a tobacco material.

BRIEF DESCRIPTION OF THE DRAWINGS

Figure 1:
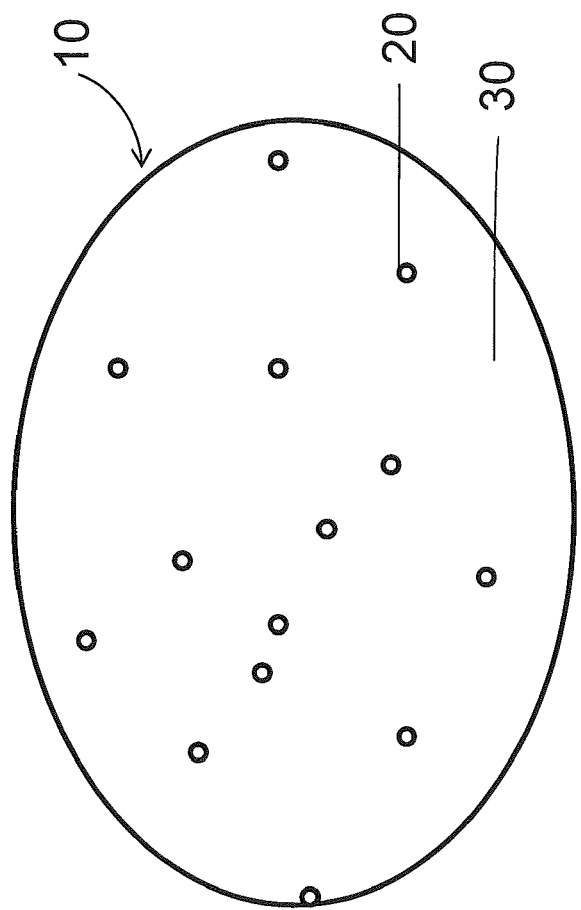

Having thus described the invention in general terms, reference will now be made to the accompanying drawings, which are not drawn to scale, and wherein:

FIG. 1 represents an exemplary orally ingestible product of the present invention comprising an unbuffered portion and a buffered portion in granule form; and FIG. 2 represents an exemplary orally ingestible product of the present invention comprising an unbuffered portion and a buffered portion in cylindrical form.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention relates to methods for the preparation of orally ingestible products (e.g., hard boiled products)

and the products provided thereby. Generally, the preparation of such products requires a step of heating sugar or a sugar substitute (referred to herein as a "sugar material") to an elevated temperature (e.g., including, but not limited to, a temperature at or above the hard crack stage). The invention is particularly applicable to orally ingestible hard boiled products comprising certain sugars, sugar substitutes, or mixtures thereof. Certain embodiments will be described primarily in reference to sugar substitute (e.g., isomalt)-based ingestible hard boiled products; however, it is understood that the invention can be readily adapted for use with other types of products. The temperatures and time periods for which the material must be heated may need to be adapted to account for the varying properties (e.g., melting/liquefying points, hard crack stages) of different sugars and sugar substitutes.

The first stage of the process typically involves applying sufficient heat to the sugar material to liquefy the sugar material. The temperature at which the sugar material is heated at this stage of the process (referred to in some cases as the first temperature herein) can be any temperature sufficient to liquefy the sugar material. To liquefy in this context refers to the movement of a material from a solid or semi-solid form to a less rigid and more malleable and fluid/flowable form (e.g., a melting or softening process). In certain embodiments, it is advantageous to heat the sugar material at this stage of the process to a temperature defined as at or above the hard crack stage. Hard crack stage is a term of art in preparing hard confectionaries, used to refer to a temperature at which there is very little water in the melted sugar material (e.g., less than about 3% by weight, less than about 2%, or less than about 1%), where the melted sugar material forms hard, brittle threads when dropped into cold water. It is important in some embodiments to allow the sugar material to reach or exceed this temperature to ensure sufficient removal of moisture from the sugar material, such that the final product exhibits a hard texture, rather than a soft, gooey texture. The temperature of the hard crack stage can vary, depending on the makeup of the sugar material. A temperature sufficient to maintain the sugar or substitute at or above the hard crack stage is generally within the range of about 150° C. to about 170° C. (about 300° F. to about 340° F.). It is noted that various additional components can be included with the sugar material; as such, reference to processing the sugar material (e.g., by heating) can, in some embodiments, refer to processing the sugar material plus optional further ingredients, as described herein.

To prepare a hard boiled product according to the inventive process, the melted sugar material is subsequently cooled (e.g., to room temperature) to obtain a solid or semi-solid form. The method of cooling can vary; for example, the cooling conditions such as the rate of cooling can vary. The cooling process generally results in the sugar material approaching or reaching a solid stage. Thus, the material thus provided and further treated according to the methods herein is a semi-solid or a solid. "Solid" and "semi-solid" are intended to have their common meaning (i.e., a material with sufficient rigidity and/or physical integrity to hold its shape, meaning the material is shape-sustaining and generally self-supporting). A semi-solid is a material that is in a phase between the melted sugar material and the solid sugar material and, for the purposes of the invention, advantageously comprises a relatively high percentage of solids. In certain embodiments, the solid is amorphous at this stage. In some embodiments, the solid is a "glassy solid," by which is meant that the solid exhibits some degree of transparency or translucency. Preferred solids described herein generally have a hard texture and preferably exhibit little to no tackiness to the touch.

Various means for heating sugar materials, e.g., at or above the hard crack stage, and cooling in order to form hard boiled products are known and can be used according to the present invention. For example, exemplary means for preparing hard boiled confectionaries are described in U.S. Pat. No. 3,114,642 to Meisel; U.S. Pat. No. 3,438,787 to DuRoss; U.S. Pat. No. 3,738,845 to Liebrand; U.S. Pat. No. 4,452,825 to Klacik et al.; U.S. Pat. No. 5,098,730 to Pepper et al., and U.S. Pat. No. 5,314,701 to Mentink et al.; which are incorporated herein by reference.

According to the invention, the solid or semi-solid thus obtained is further treated. In certain aspects of the invention, one or more ingredients are introduced into the sugar material following the cooling step. The ingredients that can be introduced into the cooled material can vary. In some embodiments, one or more of the ingredients can be viewed as temperature sensitive, meaning those ingredients otherwise would be difficult to incorporate within a hard boiled product during the initial heating step because those ingredients cannot withstand the high temperature and/or extended heating times associated with the typical methods for preparing hard boiled products. Thus, for purposes of the invention, reference to a temperature sensitive ingredient refers to an ingredient that can undergo evaporation or decomposition, participate in formation of undesirable byproducts, or otherwise alter the hard boiled composition in an undesirable manner when subjected to an elevated temperature, such as the elevated temperature experienced by a sugar material heated to its hard crack stage. Such ingredients may undergo detrimental changes at elevated temperatures, including, but not limited to, scorching, charring, decomposition, degradation, dissociation, oxidation, denaturing, polymerization or other chemical reactions, changes in physical state, or combinations thereof. In certain embodiments, the temperature sensitive ingredient introduced into the cooled material is selected from buffering agents, flavorings, and/or pharmaceutically active ingredients.

The means by which the ingredients are introduced into the material following the cooling step can vary. The ingredients may be added to the sugar material following the cooling step while the sugar material is in cooled form or may be added before, during, or after a subsequent heating step, while the sugar material is in liquefied form.

In some embodiments, the cooled sugar material is processed to provide it in a form so as to facilitate mixing with the one or more ingredients. It can be processed, for example, prior to being mixed with the one or more ingredients or during the mixing process. For example, in certain embodiments, the cooled sugar material is provided in pieces to allow it be mixed more effectively with the ingredients. The size of the pieces can vary from relatively large pieces (e.g., squares, blocks, cubes, spheres, or the like) to particulate sizes (e.g., powders or granules). In certain embodiments, the cooled sugar material is provided in particulate form, e.g., by grinding or pulverizing the solid or semi-solid sugar material. The grinding step can be done using any type of equipment capable of subdividing a solid material. For example, the cooled sugar material can be comminuted, ground or pulverized into a powder type of form using equipment and techniques for grinding, milling, or the like. Exemplary equipment includes, but is not limited to, hammer mills, cutter heads, air control mills, or the like. The size and shape of the particles of the particulate material can vary. Advantageously, the cooled material is ground to particles having an average particle diameter of about 1000 µm or less, about 500 µm or less, about 100 µm or less, about 50 µm or less, about 10 µm or less, or about 1 µm or less. In other embodiments, the sugar material and the additional ingredients can be combined after the sugar material is again liquefied in a subsequent heating step described below. The form of the ingredients at the time of the combination can vary, but typically such ingredients are added to the sugar material in solid (e.g., particulate) or liquid form.

The cooled sugar material can be mixed with the one or more ingredients by any means capable of combining such components. For example, the components can be mixed with industrial-scale mixers or agitators or can be mixed by hand. The mixing is preferably conducted at or near room temperature. Advantageously, a homogeneous or near-homogeneous mixture is thus provided.

In certain embodiments, following mixing, the resulting mixture of the sugar material, the one or more temperature sensitive ingredients and any other optional ingredients is subjected to the application of heat. It has been surprisingly discovered that a sugar material previously heated to its hard crack stage to obtain a desirably glassy solid form can be subsequently liquefied at much lower temperatures without losing the desired hard boiled solid characteristics. Thus, according to the invention, the ability to heat the sugar material in a subsequent step at a lower temperature (referred to herein as the second temperature) provides an advantageous opportunity to mix the sugar material in liquid form with one or more temperature sensitive ingredients without significant degradation of the temperature sensitive ingredient, while still maintaining desirable characteristics associated with hard boiled products of this type.

In certain embodiments, the mixture liquefies at a relatively low temperature and in a relatively short period of time. The time and temperature at which the mixture is heated can vary, but typically are such that: a) the time for which the mixture is heated to an elevated temperature is less than that required using traditional preparation techniques; and/or b) the temperature at which the mixture is heated is lower than the first temperature at which the sugar material is heated. For example, the temperature may, in some embodiments, be lower than the hard crack stage of the sugar material. The heat required to provide the mixture in liquefied form thus may be less than the heat required to provide the initial sugar material in liquefied form. This is particularly beneficial for volatile components, which may evaporate or degrade to some degree when added to a mixture at elevated temperature. In traditional hard boiled processing techniques, ingredients are typically introduced along with the sugar material prior to heating to the hard crack stage or while maintaining the sugar material at or near the hard crack stage.

For example, the hard crack stage of isomalt is 165° C. (330° F.), and this temperature can the first temperature, and the second temperature in certain embodiments is about 160° C. or less, about 150° C. or less, about 140° C. or less, about 130° C. or less, about 120° C. or less, about 110° C. or less, or about 105° C. or less. Typically, the second temperature is between about 60° C. and about 150° C., more often about 60° C. to about 120° C., or about 70° C. to about 100° C. The heating time can be, for example, about 30 minutes or less, about 20 minutes or less, about 15 minutes or less, about 10 minutes or less, about 8 minutes or less, about 7 minutes or less, about 6 minutes or less, about 5 minutes or less, about 4 minutes or less, or about 3 minutes or less.

The difference in the amount of heat introduced into the material during each of the two heating steps can also be characterized in terms of a temperature differential. For example, the difference between the first temperature (i.e., the temperature to which the sugar material is heated in the first step) and the second temperature (i.e., the temperature to which the sugar material admixed with one or more temperature sensitive ingredients is heated in the subsequent heating step) can be at least about 10° C., or at least about 20° C., or at least about 30° C., or at least about 40° C., or at least about 50° C. In certain embodiments, the temperature difference is no more than about 80° C., or no more than about 70° C., or no more than about 60° C.

Advantageously, the mixture is heated until the material reaches a melted/liquefied stage, at which point the material is cooled. Preferably, the mixture is immediately cooled (e.g., immediately upon reaching the liquefied stage) to give a solid. Surprisingly, even at relatively high temperatures, the mixture is liquefied in a short amount of time and thus, temperature sensitive ingredients therein can experience fewer detrimental effects (e.g., decomposition, change of physical state, denaturing, and the like). Thus, the ingredients within the mixture (e.g., including, but not limited to, temperature sensitive ingredients) are, in some embodiments, exposed to a relatively low elevated temperature and/or are exposed to an elevated temperature for only a brief period of time. In certain embodiments, the time and temperature to which the mixture is heated is advantageously such that it is insufficient to cause decomposition and/or evaporation of the one or more ingredients. For example, in certain embodiments, the time and temperature are such that they result in little to no decomposition of a buffering agent (e.g., a carbonate buffer). Although not intending to be limited by theory, it is believed that the second temperature at which the mixture is heated and the heat to which the mixture is exposed is insufficient to change the chemical nature of the mixture to any significant degree. For example, the mixture is advantageously exposed to heat sufficient to liquefy the mixture, but not sufficient to burn, char, oxidize, polymerize, degrade, evaporate, denature, or decompose the components thereof to any significant degree.

As noted above, the one or more temperature sensitive ingredients can be incorporated by mixing with the sugar substitute at various stages of the process. As noted above, the one or more temperature sensitive ingredients can be incorporated by mixing them with the sugar material in cooled form (i.e., before the second heating step) but can also be incorporated by mixing them with the sugar material during or after the second heating step. For example, the one or more temperature sensitive ingredients can be added during the second heating step (i.e., after the sugar material has been heated to the first temperature and cooled). It can be added, for example, during the second heating step when the sugar substitute is sufficiently liquefied to allow for mixing or may be added when the heating has ceased and the sugar substitute is cooling, but is still sufficiently liquefied to allow for mixing. Preferably, the physical state of the sugar material at the point of incorporation of the one or more temperature sensitive ingredients is such that it will allow the provision of an intimate mixture between the components before a cooled solid is formed. In fact, the production of an intimate mixture between the sugar material and the one or more temperature sensitive ingredients is an advantageous feature of the method, whether the one or more temperature sensitive ingredients are added to the sugar material while the sugar material is in solid or liquefied form.

Following the second heating step, the mixture is subsequently cooled to give an orally ingestible product (e.g., a hard boiled product). If desired, the liquefied mixture can be placed in a mold (or plurality of molds) having a desired final product shape such that the final cooled solid conforms to a desired shape. Notably, the solid product that is formed after the mixture has been treated according to the multi-stage heating method described herein (e.g., heated to an elevated temperature, e.g., the hard crack stage; cooled to a solid; combined with ingredients; reheated to a second temperature; and cooled) is a solid that can, in certain embodiments, be comparable in appearance and texture to the solid formed following the initial cooling step (i.e., the solid that is obtained after the sugar material has been initially heated, e.g., to the hard crack stage). For example, the solid may in some embodiments be a glassy solid. The solid in certain embodiments has a hard texture and preferably exhibits little to no tackiness to the touch.

Various modifications and additions to the method described herein are also intended to be encompassed within the present invention. For example, in some embodiments, a mixture of the sugar material and a temperature sensitive ingredient can be directly introduced into molds while in solid form (i.e., prior to the second heating step) and the second heating step can be conducted with the material within these molds. Various types of molds may be used in the process, such as, for example, starch molds, starchless molds, plastic tray molds, metallic tray molds, neoprene tray molds, etc. Accordingly, upon cooling, the product obtained can be removed from the mold and maintains the shape and size of the mold used. In some instances, the product mixture may be allowed to cool at refrigerated or below ambient temperatures.

The product can be treated, processed, and/or used in other ways, for example, by using the composition as a coating for another material such as by manually forming the product mixture into a desired shape at an appropriate stage of the cooling process; by casting the product mixture as a sheet and breaking it into pieces, or by dipping another material in the liquefied product mixture). The size, shape, and form of the orally ingestible hard boiled product produced according to the methods provided herein can vary widely.

Although it is beneficial to add certain additional ingredients in the manner described above, it is noted that not all additional components must be added in this way. For example, some additional components to be included within a given ingestible product formulation can withstand elevated temperatures and/or extended periods of heating. Such components may be combined with the sugar and/or sugar substitute at any stage of the process, including prior to heating the sugar or sugar substitute to the hard crack stage, while the sugar or sugar substitute is at the hard crack stage; at a certain point during the initial cooling step, before, during, or just after the mixing step, or during the heating and/or cooling of the final solid mixture. Thus, various components can be added at various stages of the process if desired.

Hard boiled products according to the present invention generally comprise at about 40% or more by weight, about 50% or more by weight, about 60% or more by weight, about 70% or more by weight, about 80% or more by weight, or about 90% or more by weight of the sugar material. Sugar as used herein has its common meaning, i.e., water-soluble crystalline carbohydrates, including but not limited to, monosaccharides (e.g., glucose, fructose, and galactose), disaccharides (e.g., sucrose, lactose, and maltose), trisaccharides, and oligosaccharides. In one exemplary embodiment, the sugar is sucrose. Sugar substitutes can be any sugarless materials (i.e., sucrose-free material) and can be natural or synthetically produced. The sugar substitute used in the invention can be nutritive or non-nutritive. For example, the sugar substitute can be a sugar alcohol. Sugar alcohols that may be useful according to the present invention include, but are not limited to, erythritol, threitol, arabitol, xylitol, ribitol, mannitol, sorbitol, dulcitol, iditol, isomalt, maltitol, lactitol, polyglycitol, and mixtures thereof. For example, in certain embodiments, the sugar alcohol is selected from the group consisting of erythritol, sorbitol, and isomalt. In one embodiment, the sugar substitute is isomalt, which is a disaccharide typically made by enzymatic rearrangement of sucrose into isomaltulose, followed by hydrogenation to give an equimolar composition of 6-O-α-D-glucopyranosido-D-sorbitol (1,6-GPS) and 1-O-α-D-glucopyranosido-D-mannitol-dihydrate (1,1-GPM-dihydrate).

In certain embodiments, the sugar material is capable of forming a glassy matrix. The formation of a glassy matrix is commonly characterized by a translucent/transparent appearance. Typically, the sugar material (e.g., sugar substitute) is substantially non-hygroscopic. Non-hygroscopic materials typically do not absorb, adsorb, and/or retain a significant quantity of moisture from the air. For example, in some embodiments, the sugar substitute exhibits a weight gain of water of less than about 50% upon exposure to conditions of 25° C., 80% relative humidity for two weeks. Typically, the sugar substitute exhibits a weight gain of less than about 30%, less than about 20%, less than about 10%, less than about 5%, less than about 2%, or less than about 1% upon exposure to conditions of 25° C., 80% relative humidity for two weeks. Non-hygroscopic materials can provide the benefit of reducing the tendency of the product to tackify upon exposure to humidity.

The other components of the orally ingestible hard boiled product can vary. For example, in some embodiments, the product contains a syrup, e.g., a sugar syrup or a sugar alcohol syrup. "Sugar alcohol syrup" as used herein is intended to refer to a thick solution of sugar alcohol in water, e.g., having greater than about 40% solids, preferably having greater than about 50% solids, greater than about 60% solids, greater than about 70% solids, or greater than about 80% solids. Typically, the solid content of the sugar alcohol syrup primarily comprises the named sugar alcohol (i.e., maltitol syrup typically comprises greater than about 80%, greater than about 85%, or greater than about 90% by weight maltitol on a dry basis). Sugar alcohol syrups are generally prepared by heating a solution of the sugar alcohol in water and cooling the mixture to give a viscous composition. The resulting syrup is typically characterized by a relatively high concentration of sugar alcohol and relatively high stability (i.e., the sugar alcohol typically does not crystallize from solution, e.g., at room temperature).

Where included, a syrup desirably is capable of affecting the re-crystallization of a melted sugar material (i.e., a sugar or sugar substitute). One exemplary sugar alcohol syrup that is particularly useful according to the present invention is maltitol syrup. Other sugar alcohol syrups can be used, including, but not limited to, corn syrup, golden syrup, molasses, xylitol, mannitol, glycerol, erythritol, threitol, arabitol, ribitol, mannitol, sorbitol, dulcitol, iditol, isomalt, lactitol, and polyglycitol syrups. Such sugar alcohol syrups can be prepared or can be obtained from commercial sources. For example, maltitol syrups are commercially available from such suppliers as Corn Products Specialty Ingredients. Although sugar alcohol syrups may be preferred, sugar syrups can, in certain embodiments, be used in place of or in combination with the sugar alcohol syrup. For example, in some embodiments, corn syrup, golden syrup, and/or molasses can be used.

The amount of sugar alcohol syrup, where added, is typically that amount required to slow recrystallization of the sugar or sugar substitute in melted form. One of skill in the art would understand the need to vary the amount of sugar alcohol syrup depending on the composition of the remaining ingredients to ensure that the recrystallization is sufficiently slow to provide a material with the desired characteristics (e.g., a desired level of translucency/transparency). Accordingly, the amount of sugar alcohol syrup can vary, but typically ranges from about 0% to about 2%, about 0.5% to about 1.5%, or about 1% by weight of the product mixture. In certain embodiments, the amount of sugar alcohol syrup is higher, for example, up to about 2% by weight of the mixture, up to about 5% by weight of the mixture, up to about 10% by weight of the mixture, or up to about 20% by weight of the mixture.

In certain embodiments, the product further comprises one or more salts. The presence of a salt in the product may act to suppress bitterness and/or enhance sweetness. Any type of salt can be used. Common table salt (NaCl) is typically used according to the present invention, but other types of salts are intended to be encompassed as well. The amount of salt added may vary, but typically ranges from 0% to about 8%, for example from about 1% to about 4% or from about 0% to about 2%, often around 1% by weight of the product. In some embodiments, a somewhat salty taste is a desirable feature of the product.

In some embodiments, the composition according to the invention also contains one or more buffering agents and/or pH adjusters (i.e., acids or bases). In some embodiments, one or more buffering agents and/or pH adjusters are added to the mixture to ensure that the final product has a pH within a desirable range. Exemplary pH ranges in such products are generally from about 6-11, and often about 7-10 (e.g., about 7 or about 8). In such embodiments, the amount of buffering agent and/or pH adjuster added to the product mixture is simply that amount required to bring the formulation to or keep the formulation at the desired pH. The amount of buffering agent and/or pH adjuster added to any given formulation can be readily calculated by one skilled in the art and may comprise, for example, about 0.5% to about 1% by weight of the mixture. It is noted that in certain embodiments, a basic pH is not necessary in the products of the present invention. Accordingly, certain products of the present invention have a pH of less than about 6 or less than about 5 (e.g., from about 4 to about 6).

Various food-grade buffering agents are known and can be used to adjust the pH of the products of the present invention. Suitable buffering agents include those selected from the group consisting of acetates, glycinates, phosphates, glycerophosphates, citrates such as citrates of alkaline metals, carbonates, hydrogen carbonates, and borates, and mixtures thereof. In certain embodiments, the buffering agent is an amino acid, as taught for example, in US Pat. Pub. No. 2008/0286341 to Andersson et al. and PCT Appl. No. WO2008/040371 to Andersson et al., which are both incorporated herein by reference. As noted therein, various amino acids and salts thereof are useful for this purpose, including, but not limited to, arginine, asparigine, glutamic acid, glutamine, glycine, histidine, isoleucine, leucine, lysine, methionine, phenylalanine, serine, threonine, valine, cysteic acid, N-glycylglycine, and ornithine. In certain embodiments, N-glycylglycine or L-lysine is added as a buffering agent. In some embodiments, an amino acid buffering agent is used in combination with another amino acid buffering agent and/or in combination with one or more non-amino acid buffering agents. In certain embodiments, the optional pH adjusting agent is a base (e.g., NaOH). In certain embodiments, the optional pH adjusting agent is a carbonate (e.g., sodium bicarbonate and/or sodium carbonate). In certain embodiments, L-lysine and NaOH are added to the compositions of the present invention.

In some embodiments, one or more additional sweeteners are added to the compositions of the present invention. The one or more additional sweeteners can comprise any natural or artificial sweetener, including, but not limited to, sugar or any of the sugar substitutes described previously. In certain embodiments, the sweetener can include glycyrrhizin, glycerol, inulin, lactitol, mabinlin, maltitol, mannitol, miraculin, monatin, monellin, osladin, pentadin, polydextrose, sorbitol, stevia, tagatose, thaumatin, acesulfame potassium, alitame, aspartame, cyclamate, dulcin, glucin, neotame, saccharin, sucralose, and combinations thereof. In certain embodiments, the sweetener comprises sucralose (1,6-Dichloro-1,6-dideoxy-β-D-fructofuranosyl-4-chloro-4-deoxy-α-D-galactopyranoside). The amount of sweetener added can vary, but is typically that amount required for a sufficiently "sweet" taste. For example, sweetener can be added to make the sweetness of the product comparable to that of sugar. In particular embodiments, sucralose is added in an amount of about 0.5% to about 2% by weight of the mixture, often in an amount of about 1% by weight of the mixture.

Various natural and/or artificial flavorants can also be added to the smokeless tobacco products of the present invention, and the character of these flavors can be described as, without limitation, fresh, sweet, herbal, confectionary, floral, fruity or spicy. Specific types of flavors include, but are not limited to, vanilla (e.g., vanillin optionally in complexed form), coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, lemon, orange, apple, peach, lime, cherry, and strawberry. See also, Leffingwill et al., Tobacco Flavoring for Smoking Products, R. J. Reynolds Tobacco Company (1972), which is incorporated herein by reference. Flavorings also can include components that are considered moistening, cooling or smoothening agents, such as eucalyptus. Flavorings can also include sensates, which can add a range of tactile, organoleptic properties to the products. For example, sensates can provide a warming, cooling, or tingling sensation. These flavors may be provided neat (i.e., alone) or in a composite (e.g., spearmint and menthol, or orange and cinnamon). Flavorants of this type can be present in an amount of from about 0.5% to about 15%, often between about 0.5% and about 1.5% by weight of the product mixture. In certain embodiments, the flavorant is present in any amount of at least about 0.5% by weight or at least about 0.75% by weight of the mixture.

Various other substances can be added to the compositions of the present invention. For example, excipients such as fillers or carriers for active ingredients, where present (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No. 10), and lubricants or processing aids (e.g, calcium stearate or magnesium stearate) are added to the compositions in certain embodiments.

In certain embodiments, it may be advantageous to incorporate one or more anti-oxidants, such as ascorbyl palmitate and/or sodium ascorbate, in a composition according to the invention. The one or more anti-oxidants may be present in a concentration of from about 0.05% to about 0.3% by weight, such as, e.g., from about 0.1% to about 0.25% or from about 0.15% to about 0.2% in the mixture.

Certain products also can have outer coatings composed of ingredients capable of providing acceptable outer coatings (e.g., an outer coating can be composed of ingredients such as carnauba wax, and pharmaceutically acceptable forms of shellacs, glazing compositions and surface polish agents). Application of a coating can be accomplished using techniques such as airless spraying, fluidized bed coating, use of a coating pan, or the like. Materials for use as a coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Orally ingestible hard boiled products prepared according to the present invention can have various types of formats and configurations, and as a result, the character, nature, behavior, consistency, shape, form, size and weight of the composition can vary. The shape of a representative composition can be generally spherical, cylindrical (e.g., ranging form the general shape of a flattened disc to the general shape of a relatively long, slender stick), helical, obloid, square, rectangular, or the like. The orally ingestible hard boiled product can, for example, have the form of a drop, lollipop, or ribbon. The shape of the composition can resemble a wide variety of pill, tablet, lozenge, capsule, and caplet types of products. See, for example, the types of lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference.

Although the products are generally described herein as orally ingestible hard boiled products, it is noted that in some embodiments, the orally ingestible hard boiled material can comprise only a portion of a product. For example, the orally ingestible hard boiled material provided by the present invention can be combined with one or more other orally ingestible formulations, which may or may not be another hard boiled formulation, e.g., to give a filled product, a striped product, a layered product, a coated product, or another composite-type ingestible product. Although generally, at least one of the formulations in such composite products is prepared according to the re-melting process described herein, it is possible that one or more additional formulations in a composite formulation is prepared in other ways (e.g., by conventional orally ingestible hard boiled product preparation methods or by other methods for preparing various ingestible confectionary products). For manners in which the hard boiled product of the invention could be combined with other product formats, see U.S. application Ser. No. 13/370,600 to Duggins et al., filed Feb. 10, 2012, which is incorporated by reference herein.

Such formulations can be combined into a composite product using methods known in the art. For example, in certain embodiments, two hemispheres are prepared (which can be the same or different formulations), heated (e.g., at about 100° C., or until they just start to melt), and the flat sides are pressed together to weld the hemispheres together. In some embodiments, multiple sheets or layers, which each may have different properties, can be made by layering cooled sheets and heating them or by separately heating cooled sheets and pressing them together to weld the layers together. Other variations to provide composite compositions would be within the knowledge of one of ordinary skill in the art and are intended to be encompassed hereby.

In certain embodiments, buffered (i.e., containing a buffering agent) and unbuffered (i.e., substantially or completely free of buffering agent) compositions are combined within an orally ingestible hard boiled product. In certain embodiments, it may be desirable to provide a substantially transparent orally ingestible hard boiled product. However, the presence of certain ingredients within the products of the invention, particularly certain buffering agents such as carbonate buffering agents, can reduce transparency such that the buffered composition can be characterized as translucent or opaque. Thus, where a buffered product is desired to have an overall substantially transparent appearance, the buffered portion of the product can be segregated into only a portion of the product unit to reduce the negative effect on transparency produced by such buffered portion of the composition. For example, granules of a buffered composition (prepared via the re-melting process described herein) can be incorporated into a non-buffered composition by admixing the buffered composition granules with a non-buffered composition melt at a temperature below the hard crack stage (e.g., during the cooling process). The resulting product will have a "speckled" appearance by virtue of the translucent or opaque buffered composition granules dispersed within the unbuffered composition. An exemplary orally ingestible product 10 having this configuration is shown in FIG. 1, where the granules of the buffered portion 20 are dispersed within the unbuffered portion 30. In this product configuration, the buffering agent in the buffered portion will be released at regular intervals as the product dissolves in the mouth of the user.

As another example, a formed unit of a buffered composition (e.g., as provided according to the re-melting process described herein) can be placed within a mold and subsequently, an unbuffered formulation can be added thereto, for example, in the form of a melt (either directly after heating the formulation to the hard crack stage or following a re-heating process as described herein) to create a multi-layered product. The relative spatial configuration of the two compositions can vary as desired by varying the size, shape, and configuration of the mold. In certain embodiments, the composite material can have a central buffered portion with a surrounding non-buffered portion. In some embodiments, the buffered and unbuffered portions are compositionally similar, with the only difference being the presence/absence of the buffer. In one advantageous product configuration, the two compositions are arranged such that both compositions are exposed on at least one exterior surface of the orally ingestible product. For example, the buffered portion may be provided in various shapes such that it extends the full width or length of the unit or the two portions can be arranged side-by-side such as in a hemispherical arrangement. A cross-sectional side view of a further example of an orally ingestible product 10 of the invention is shown in FIG. 2, wherein a cylindrical buffered portion 50 is present in the interior of the product substantially encased in the unbuffered portion 60, except for the extreme ends of the cylinder which reach the exterior surface of the product. In such embodiments, both formulations advantageously dissolve at the same rate in the user's oral cavity, allowing the buffer to be released during substantially the entire dissolution process.

Advantageously, the buffered portion is a minimum component of the orally ingestible product. For example, it may comprise less than about 2% by volume, less than about 5% by volume, less than about 10% by volume, less than about 20% by volume, less than about 30% by volume, less than about 40% by volume, or less than about 50% by volume of the orally ingestible product. The buffered portion generally is translucent or opaque. Advantageously, the unbuffered portion may exhibit a high degree of translucency and/or transparency. Typically, the buffered portion exhibits a darker appearance. Accordingly, this embodiment provides an aesthetically pleasing appearance as well as functional attributes associated with the buffering agent.

This embodiment may be particularly applicable with regard to products comprising one or more components that are advantageously buffered such as, for example, nicotine compounds (e.g., nicotinic salts). As described in further detail herein, nicotine components may advantageously be incorporated in salt form and converted to unprotonated form during use (i.e., within the user's mouth). Products comprising an unbuffered and buffered portion may advantageously further comprise such a compound.

The amount of material contained within each piece (e.g., each unit of lozenge type of product) can vary. For example, a representative unit for lozenge products generally weighs at least about 100 mg, often at least about 200 mg, and frequently at least about 300 mg; while the weight of a representative unit for such products generally does not exceed about 1.5 g, often does not exceed about 1 g, and frequently does not exceed about 0.75 g.

In some embodiments, the orally ingestible hard boiled products provided according to the methods of the present invention are food products. For example, the ingestible products can be confectionary compositions (e.g., hard candies, lollipops, and the like).

In some embodiments, the ingestible products provided according to the methods of the present invention can contain one or more pharmaceutically active ingredients. Such products can be, in some embodiments, pharmaceutical compositions that can be used to treat various conditions. In such embodiments, carriers and/or excipients are generally included that are pharmaceutically acceptable, i.e., conventionally used in the art to facilitate the storage, administration, and/or the healing effect of an active agent.

For example, the invention can, in certain embodiments, provide throat lozenges can comprise menthol, benzocaine, pectin, dextromethorphan, dyclonine hydrochloride, other antiseptics (e.g., amylmetacresol, 2,4-dichlorobenzyl alcohol, or hexylresorcinol) and/or various oils (e.g., peppermint or eucalyptus oil). In some embodiments, pharmaceutically active ingredients for oral malodour (halitosis), anti-inflammatory compounds, antibiotic compounds, antihistamines, decongestants, anti-nauseants, and sedatives can be included within orally ingestible hard boiled products according to the present invention. The invention can, in certain embodiments, provide lozenges that contain one or more vitamins, minerals, nutritional supplements, and/or botanicals (e.g., vitamin A, vitamin C, vitamin D, vitamin E, vitamin B12, vitamin K, iron, zinc, copper, selenium, chromium, iodine, calcium, selenium, ginger, licorice, peppermint, cinnamon, horehound, hyssop, ginseng, ginko biloba, St. Johns Wort, valerian, and/or Echinacea).

In certain embodiments, the optional active ingredient comprises a nicotinic compound. As used herein, "nicotinic compound" refers to naturally occurring or synthetic nicotine unbound from a plant material, meaning the compound is at least partially purified and not contained within a plant structure such as a tobacco leaf. Most preferably, nicotine is naturally-occurring and obtained as an extract from a *Nicotiana* species (e.g., tobacco). Exemplary types of tobacco and manners of processing the tobacco are set forth in U.S. Pat. No. 7,946,295 to Brinkley et al. and patent application Ser. No. 13/095,277 to Byrd et al., which are incorporated herein by reference.

Nicotinic compounds of the invention can include nicotine in free base form, salt form, as a complex, or as a solvate. See, for example, the discussion of nicotine in free base form in US Pat. Pub. No. 2004/0191322 to Hansson, which is incorporated herein by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12, 43-54 (1983). Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate) chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotinic compound is in the form of a salt with an organic acid moiety, including, but not limited to, levulinic acid as discussed in U.S. patent application Ser. No. 12/769, 335 and International Application No. PCT/US2011/033928, both to Brinkley et al., which are incorporated herein by reference.

In one embodiment, the nicotinic compound is sorbed onto a porous particulate carrier material, such as microcrystalline cellulose (MCC) prior to incorporation within the compositions of the invention. In one embodiment, the MCC materials used in the invention have an average particle size range of about 15 to about 250 microns. Exemplary MCC materials include various grades of AVICEL® and VIVACEL® materials. See, for example, US Pat. Pub. No. 2004/0191322 to Hansson, which is incorporated by reference herein. In certain embodiments, multiple forms of nicotinic compounds could be sorbed onto the particulate carrier, including any of the various nicotinic compound combinations discussed herein. In some embodiments, the nicotinic compound and, optionally, an organic acid moiety can be sorbed onto the particulate carrier by, for example, dissolving the nicotinic compound (and, optionally, an organic acid moiety) in a hydrophilic solvent (such as water, alcohol, or mixtures thereof) and combining the solution with the particulate carrier, followed by drying to remove the solvent. The particulate carrier material with the sorbed nicotine and, optionally, organic acid moiety, can be combined with other carriers or excipients in order to provide a composition adapted for oral delivery of the active ingredient.

Advantageously, in some embodiments, nicotine-containing products are buffered. In such embodiments, it may be desirable to keep the nicotinic compound in a salt form for stability during manufacturing and storage, but allow for buffering during use. It is desirable to keep nicotine in a salt form prior to use of a nicotine-containing product. Salts generally have lower vapor pressure than unprotonated nicotine, so that unprotonated nicotine more readily is lost due to heating during manufacture. Similarly, at lower temperatures, unprotonated nicotine is more readily evaporated and can turn clear packaging of the product yellow, giving the appearance of an old or outdated product. Unprotonated nicotine also can transfer from a product to packaging material more readily than nicotinic salts. Nicotine salts also are more chemically stable to oxidation than the unprotonated form.

However, it is desirable to provide the nicotine in unprotonated form in use, as the salt form will not transfer across the buccal membrane. Providing a nicotine salt (e.g., on a support) within a product and providing appropriate buffers therewith allows for a product that is stable during storage (as the nicotine is in salt form), but which forms unprotonated nicotine in use (e.g., upon contact with saliva in the user's mouth).

The amount of nicotine within each dosage piece or unit typically is at least about 0.5 mg, generally is at least 1 mg, often is at least about 1.5 mg, and frequently is at least about 2 mg; while the amount of nicotine within each piece typically does not exceed about 10 mg, generally does not exceed about 8 mg, often does not exceed about 6 mg, and frequently does not exceed about 5 mg, calculated as nicotine base. Exemplary types of such products can incorporate about 2 mg, about 2.5 mg, about 3 mg, about 3.5 mg and about 4 mg of nicotine per piece or unit, calculated as nicotine base. Further details of exemplary nicotine-containing products are provided, for example, in U.S. patent application Ser. No. 13/240,500 to Holton Jr. et al., filed Sep. 22, 2011, which is incorporated herein by reference in its entirety.

In some embodiments, the orally ingestible hard boiled products provided according to the methods of the present invention are smokeless tobacco products. Accordingly, the hard boiled products can, in some embodiments, comprise a tobacco material, e.g., in the form of particulate tobacco and/or a tobacco extract. The tobacco material can vary. For example, various types of tobacco can be used; various portions of the tobacco plant can be used; and various harvesting, drying, curing, and/or processing methods can be used according to the invention, as described, for example, in U.S. patent application Ser. No. 13/370,600 to Duggins et al., filed Feb. 10, 2012, which is incorporated herein by reference in its entirety.

In certain embodiments, the orally ingestible hard boiled products comprise a tobacco extract that is treated (e.g., by ultrafiltration, microfiltration, nanofiltration, size exclusion chromatography, reverse osmosis, or combinations thereof) as described, for example, in U.S. patent application Ser. No. 13/240,525 to Holton Jr. et al., filed Sep. 22, 2011, which is incorporated herein by reference. Treated extracts, as provided therein, generally exhibit improved clarity as compared with untreated extracts, due to the removal of certain high molecular weight Maillard browning polymers, proteins, polysaccharides, certain pigments, and bacteria.

The treating (e.g., filtering) can, for example, comprise passing an aqueous tobacco extract through a membrane or series of semipermeable membranes. The membrane can be of any type, such as plate-and-frame (having a stack of membranes and support plates), spiral-wound (having consecutive layers of membrane and support material rolled up around a tube), tubular (having a membrane-defined core through which the feed flows and an outer, tubular housing where permeate is collected), or hollow fiber (having several small diameter tubes or fibers wherein the permeate is collected in the cartridge area surrounding the fibers). The membrane can be constructed of various materials. For example, polysulfone, polyethersulfone, polypropylene, polyvinylidenefluoride, and cellulose acetate membranes are commonly used, although other materials can be used without departing from the invention described herein.

Ultrafiltration membranes are available in a wide range of pore sizes (typically ranging from about 0.1 to about 0.001 microns). Membranes are more typically described by their molecular weight cutoffs. Ultrafiltration membranes are commonly classified as membranes with number average molecular weight cutoffs of from about $10^3$ Da to about $10^5$ Da. In practice, compounds with molecular weights above the molecular weight cutoff are retained in the retentate, and the compounds with molecular weights below the cutoff pass through the filter into the permeate. Ultrafiltration methods typically are not capable of removing low molecular weight organic compounds and ions. Nanofiltration is a filtration method wherein generally, the molecular weight cutoff of the filters is generally within the range of about 100 Da to about 1000 Da. In other words, nanofilters that allow only components of the tobacco extract having molecular weights below about 100 Da, below about 250 Da, below about 500 Da, below about 750 Da, or below about 1000 Da can, in certain embodiments, be used to clarify the tobacco extract according to the invention.

Ultrafiltration and nanofiltration may comprise a cross-flow separation process. The liquid stream to be treated (feed) flows tangentially along the membrane surface, separating into one stream that passes through the membrane (permeate) and another that does not (retentate or concentrate). The operating parameters of the filtration system can be varied to achieve the desired result. For example, the feed mixture to be filtered can be brought into contact with the membrane by way of applied pressure. The rate of permeation across the membrane is directly proportional to the applied pressure; however, the maximum pressure may be limited. The flow velocity of the mixture across the membrane surface can be adjusted. Temperature can also be varied. Typically, permeation rates increase with increasing temperature.

Commercial nanofiltration and ultrafiltration systems are readily available and may be used for the filtration methods of the present invention. For example, commercial suppliers such as Millipore, Spectrum® Labs, Pall Corporation, Whatman®, Porex Corporation, and Snyder Filtration manufacture various filter membranes and cartridges, and/or filtration systems (e.g., tangential flow filtration systems). Exemplary membranes include, but are not limited to, Biomax® and Ultracel® membranes and Pellicon® XL cassettes (from Millipore), Microkros®, Minikros®, and KrosFlo® Hollow Fiber Modules (from Spectrum® Labs), and Microza filters and Centramate,™ Centrasette,™ Maximate™, and Maxisette™ Tangential Flow Filtration Membrane Cassettes. Commercially available filtration systems include, but are not limited to, Millipore's Labscale™ Tangential Flow Filtration (TFF) system and Spectrum® Labs' KrosFlo® and Mini-Kros® Tangential Flow Filtration Systems.

Although ultrafiltration can be used to clarify a tobacco extract according to the present invention, it is noted that, in certain embodiments, a more or less rigorous process can be used. In certain embodiments, nanofiltration is used, which may be capable of removing a greater number of compounds (i.e., compounds with lower molecular weights) from a tobacco extract than ultrafiltration. In certain embodiments, a treated tobacco extract can be characterized by a low tobacco-specific nitrosamine content (e.g., about 150 ng/g or less)

and/or a low benzo[a]pyrene content (e.g., about 1 ng/g or less), based on the weight of the treated extract.

Advantageously in some embodiments, the treated tobacco extract generally comprises fewer high molecular weight components than tobacco extract that has not been treated in this way. In certain embodiments, the treated tobacco extract can be characterized as translucent and/or transparent. As used herein, "translucent" or "translucency" refers to the ability to allow some level of light to travel therethrough diffusely. In certain embodiments, the treated extract can have such a high degree of clarity that it can be classified as "transparent" or exhibiting "transparency," which is defined as a material allowing light to pass freely through without significant diffusion. The clarity of the treated extract is generally such that there is some level of translucency as opposed to opacity (which refers to materials that are impenetrable by light).

The improvement in clarity of the treated extract over a non-treated extract can be quantified by any known method. For example, optical methods such as turbidimetry (or nephelometry) and colorimetry may be used to quantify the cloudiness (light scattering) and the color (light absorption), respectively, of the clarified tobacco extract. Translucency can also be confirmed by visual inspection by simply holding the treated extract up to a light source and determining if light travels through the material or product in a diffuse manner. This also applies to evaluation of translucency or transparency of the buffered and unbuffered portions of a product as described above. The treated extract can be stored and/or used in solid form (e.g., spray-dried or freeze-dried form), in liquid form, in semi-solid form, or the like.

Although in some embodiments, a tobacco extract is used directly, it may be desirable to heat treat an extract. This thermal treatment can be conducted, in some embodiments, in combination with treatment (e.g., ultrafiltration) as described above. For example, an extract can be heat treated before the ultrafiltration, after the ultrafiltration, or both before and after the ultrafiltration. For example, a tobacco material can be thermally treated by mixing the tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents (e.g., hydrogen peroxide), oxidation catalysts, plant extracts, and combinations thereof, to form a moist tobacco mixture; and heating the moist tobacco mixture at a temperature of at least about 60° C. to form a heat-treated tobacco mixture. In one embodiment, the tobacco extract is heat treated in the presence of water, NaOH, and an additive (e.g., lysine) at about 88° C. for about 60 minutes. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference. In certain embodiments wherein a heat-treated tobacco extract is used in a smokeless tobacco product of the present invention, the product can be characterized by very low acrylamide content. For example, in some embodiments, the smokeless tobacco product is characterized by an acrylamide content of less than about 500 ppb (ng/g), less than about 400 ppb, less than about 300 ppb, less than about 200 ppb, or less than about 100 ppb.

According to certain embodiments of the invention, the amount of tobacco material within the orally ingestible hard boiled product can vary. For example, tobacco extract can be provided in varying concentrations, which can affect the amount of extract included in the mixture. The amount of extract is at least about 0.5%, generally at least about 1%, often at least about 1.5%, often at least about 2%, often at least about 2.5%, and frequently at least about 3% by weight of the product mixture. In certain embodiments, the amount of extract is at least about 4%, at least about 5%, at least about 6%, or at least about 7% by weight of the product mixture. The amount of treated tobacco extract added to the product mixture is typically not more than about 20%. Exemplary types of such products can incorporate about 3% by weight, about 4% by weight, about 4.5% by weight of the mixture, or about 7.5% by weight of the mixture.

Further ingredients can be admixed with, or otherwise incorporated within, the smokeless tobacco compositions according to the invention, such as other ingredients described herein. The additional ingredients can be artificial, or can be obtained or derived from herbal or biological sources. If desired, the ingredients can be microencapsulated as set forth in US Patent Appl. Pub. No. 2008/0029110 to Dube et al., which is incorporated by reference herein. In addition, exemplary encapsulated ingredients are described, for example, in WO 2010/132444 A2 to Atchley, which is also incorporated by reference herein.

The following examples are provided to illustrate further the present invention, but should not be construed as limiting the scope thereof. Unless otherwise noted, all parts and percentages are by weight.

EXPERIMENTAL

The present invention is more fully illustrated by the following examples, which are set forth to illustrate the present invention and are not to be construed as limiting thereof. In the following examples, g means gram, L means liter, mL means milliliter, and Da means daltons. All weight percentages are expressed on a dry basis, meaning excluding water content, unless otherwise indicated.

Example 1

Preparation of Hard Boiled Tobacco Extract-Containing Product with Buffer

Isomalt glass is prepared by heating isomalt (92.41 g) in excess of 166° C. (330° F.), cooling the melted isomalt to below 149° C. (300° F.), mixing an aqueous tobacco extract comprising 50% solids (7.55 g of extract) into the isomalt, casting the mixture onto a parchment sheet and cooling the mixture to room temperature, giving a solid with a glassy appearance (light brown and transparent). The cooled glassy solid is ground into a powdered glass.

A portion of the powdered glass (40 g) is blended at room temperature with a carbonate buffer mixture (0.599 g, 2% of the powder weight) comprising 97% sodium bicarbonate and 3% sodium carbonate. The blended powder material is transferred to a mold and the mold is placed into an oven at 102° C. for 3 minutes and removed. The resulting material is in a solid (melted) form and is light yellow and opaque. There is no evidence of the decomposition of the bicarbonate to give carbon dioxide. The pH of a 5% solution of this blended powder material is 7.02, and the pH of a 5% solution of the powdered glass is 4.18.

Example 2

Evaluation of Higher Sodium Carbonate Content and Longer Heating Time

An additional 0.620 g of the carbonate buffer mixture described in Example 1 and an additional 0.084 g sodium carbonate are added to 30 g of the blended powder material of Example 1. The pH of a 5% solution in water was 7.70. An additional 0.080 g sodium carbonate are added and the pH of a 5% solution in water was 8.23. A portion of this powdered blend is transferred to a mold and the mold is placed into an oven at 102° C. for 3 minutes and removed. The resulting material is in a solid (melted) form and is light yellow and opaque. Another portion of the powdered blend is transferred to a mold and the mold is placed into an oven at 102° C. for 6 minutes and removed. The resulting material is in a solid (melted) form and is light yellow and opaque and again shows no evidence of decomposition of the bicarbonate.

Example 3

Hard Boiled Tobacco Extract-Containing Product without Buffer

A portion of the powdered glass prepared according to Example 1 is transferred to a mold and the mold is placed into an oven at 102° C. for 3 minutes and removed. The resulting material is in a solid (melted) form and exhibits the same visual characteristics as the melted and cooled tobacco extract-containing isomalt, i.e., a glassy appearance (light brown and transparent).

Many modifications and other aspects of the disclosure set forth herein will come to mind to one skilled in the art to which the disclosure pertain s having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

What is claimed:

1. A method of preparing an orally ingestible product, comprising:
   i) heating a sugar material to a first temperature sufficient to liquefy the sugar material and form a first liquefied sugar material;
   ii) cooling the first liquefied sugar material to provide a cooled sugar material having a solid or semi-solid form;
   iii) heating the cooled sugar material to a second temperature, which is lower than the first temperature, to provide a second liquefied sugar material;
   iv) combining the sugar material with one or more temperature sensitive ingredients before, during, or after said heating step iii), but after said cooling step ii), such that an intimate mixture of the second liquefied sugar material and the one or more temperature sensitive ingredients is provided;
   v) cooling the intimate mixture to form an orally ingestible product.

2. The method of claim 1, wherein the sugar material comprises a sugar alcohol.

3. The method of claim 1, wherein the sugar material comprises isomalt.

4. The method of claim 1, wherein the first temperature is a temperature at or above the hard crack stage of the sugar material.

5. The method of claim 1, wherein the first temperature is about 150° C. to about 170° C.

6. The method of claim 1, wherein the second temperature is about 60° C. to about 150° C.

7. The method of claim 6, wherein the second temperature is about 60° C. to about 120° C.

8. The method of claim 1, wherein the difference between the first temperature and the second temperature is at least about 10° C.

9. The method of claim 8, wherein the difference between the first temperature and the second temperature is at least about 30° C.

10. The method of claim 9, wherein the difference between the first temperature and the second temperature is at least about 50° C.

11. The method of claim 1, wherein the first temperature is about 150° C. to about 170° C., the second temperature is about 60° C. to about 150° C., and the difference between the first temperature and the second temperature is at least about 10° C.

12. The method of claim 11, wherein the difference between the first temperature and the second temperature is at least about 30° C.

13. The method of claim 1, wherein the one or more temperature sensitive ingredients are selected from the group consisting of buffering agents, flavorings, pharmaceutically active ingredients, and combinations thereof.

14. The method of claim 1, wherein the temperature sensitive ingredient is a carbonate buffering agent or a nicotinic compound.

15. The method of claim 14, wherein the temperature sensitive ingredient is sodium carbonate, sodium bicarbonate, or a combination thereof.

16. The method of claim 14, wherein the nicotinic compound is in the form of a nicotine salt.

17. The method of claim 14, wherein the nicotinic compound is sorbed onto a porous particulate carrier.

18. The method of claim 1, wherein the intimate mixture further comprises a tobacco material.

19. The method of claim 18, wherein the tobacco material comprises a tobacco extract or particulate tobacco.

20. The method of claim 1, wherein the orally ingestible product is in the form of a smokeless tobacco product.

21. The method of claim 1, further comprising the step of subdividing the cooled sugar material of step ii) into a plurality of pieces, and wherein the combining step comprises mixing the subdivided, cooled sugar material with the one or more temperature sensitive ingredients.

22. The method of claim 21, wherein the step of subdividing the cooled sugar material comprises grinding the cooled sugar material to provide a particulate material.

23. The method of claim 1, further comprising the step of introducing the intimate mixture into a mold prior to cooling such that the orally ingestible product is formed into a desired shape.

24. A method of preparing an orally ingestible product, comprising:
   i) applying heat to a sugar material sufficient to liquefy the sugar material and form a first liquefied sugar material;
   ii) cooling the first liquefied sugar material to provide a cooled sugar material having a solid or semi-solid form;
   iii) applying heat to the cooled sugar material to provide a second liquefied sugar material, the amount of heat applied to the cooled sugar material being less than the amount of heat applied in step i);
   iv) combining the sugar material with one or more temperature sensitive ingredients before, during, or after said step of applying heat to the cooled sugar material iii), but after said cooling step ii), such that an intimate mixture of the second liquefied sugar material and the one or more temperature sensitive ingredients is provided; and v) cooling the intimate mixture to form an orally ingestible product.

25. The method of claim 24, wherein the sugar material comprises isomalt.

26. The method of claim 24, wherein the step of applying heat to a sugar material in step i) comprises heating the sugar material at or above the hard crack stage of the sugar material.

27. The method of claim 24, wherein difference in heat applied in step i) and step iii) is characterized by a difference in temperature of the material heated in each step of at least about 10° C.

28. The method of claim 27, wherein the difference in temperature of the material heated in each step is at least about 30° C.

29. The method of claim 24, wherein the one or more temperature sensitive ingredients are selected from the group consisting of buffering agents, flavorings, pharmaceutically active ingredients, and combinations thereof.

30. The method of claim 29, wherein the temperature sensitive ingredient is a carbonate buffering agent.

31. The method of claim 24, wherein the intimate mixture further comprises a tobacco material.

32. The method of claim 24, wherein the orally ingestible product is in the form of a smokeless tobacco product.

33. The method of claim 24, further comprising the step of subdividing the cooled sugar material of step ii) into a plurality of pieces, and wherein the combining step comprises mixing the subdivided, cooled sugar material with the one or more temperature sensitive ingredients.

34. The method of claim 1, wherein the one or more temperature sensitive ingredients comprises a temperature sensitive buffering agent, and wherein the orally ingestible product is formed by combining the intimate mixture comprising the temperature sensitive buffering agent with a second non-buffered composition comprising a sugar material to form a multi-layered product.

35. The method of claim 34, wherein the intimate mixture and the second non-buffered composition are combined in liquefied form and then cooled to form the multi-layered product.

36. The method of claim 34, wherein both the intimate mixture comprising the temperature sensitive buffering agent and the second non-buffered composition of the multi-layered product are exposed on the surface of the product.

37. The method of claim 34, wherein one or both of the intimate mixture comprising the temperature sensitive buffering agent and the second non-buffered composition further comprise a pharmaceutically active ingredient.

38. The method of claim 34, wherein one or both of the intimate mixture comprising the temperature sensitive buffering agent and the second non-buffered composition further comprise a tobacco material.

* * * * *